US00PP09203P

United States Patent [19]

Klemm

[11] Patent Number: Plant 9,203

[45] Date of Patent: Jul. 18, 1995

[54] GERANIUM NAMED 'KLEGRAND'

[75] Inventor: Siegfried Klemm, Stuttgart, Germany

[73] Assignee: Klemm & Sohn, Stuttgart-Muhlhausen, Germany

[21] Appl. No.: 173,419

[22] Filed: Dec. 23, 1993

[51] Int. Cl.[6] ..... A01H 5/00

[52] U.S. Cl. ..... Plt./87.12

[58] Field of Search ..... Plt. 87.12

*Primary Examiner*—James R. Feyrer

[57] ABSTRACT

A new geranium cultivar particularly distingushed by its early appearing lavender-pink flowers with red that appear numerously on upright cluster stems over medium green foliage, the cultivar growing to a height of between 220–240 mm.

1 Drawing Sheet

BACKGROUND OF THE NEW PLANT

The present invention comprises a new and distinct cultivar of geranium, botanically known as *Pelargonium zonale—Hybride.* The new cultivar is propagated from cuttings resulting from the cross of plants in our E-generation of plants, which are not commercially available. More specifically, this new plant is a product of a planned breeding program intended to creat new geranium cultivars with pink or lavender flower color, remarkable precocity, high floral richness, or very upright standing cluster stems. As part of this breeding program seeds were collected from seedlings that had some of these characteristics from the E-generation of plants. These seedlings were grown into plants and Klegrand was selected for further propagation.

This new cultivar was created in 1989 in Stuttgart, Germany and has been repeatedly asexually reproduced by cuttings in Stuttgart, Germany, and Teneriffe, Italy, over a four year period. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to the R.H.S. Color Chart of The Royal Horticultural Society of London.

THE PLANT

Classification:

*Botanical.—Pelargonium zonale*—Hybride.

*Commercial.*—Zonal geranium.

Parentage:

*Seed parent.*—An unnamed, unnumbered, unrecorded selection from seedlings resulting from the E-generation of our planned breeding program. The seed parent is not commercially available.

*Pollen parent.*—An unnamed, unnumbered, unrecorded selection from seedlings resulting from the E-generation of our planned breeding program. The pollen parent is not commercially available.

Form: Bushy.

Shape: Round.

Height: 220–240 mm in September.

Stem length: 160–170 mm in June and 220–240 in September.

Number of stems per stalk: 8–9.

Number of stalks per plant: About 14.

Internode length: 6–10 mm.

Growth rate: The time from propagation in January to the day when you can sell the bloom is short: in 1990, Apr. 5, in 1991, Apr. 2 and in 1922, Apr. 2.

Strength: Good cutting producer for propagation, and the plant performs very well after shipping as a rooted or unrooted cutting.

Foliage: Very healthy, medium green, satin, small, dense.

Leaves: Abundant quantity.

Size: 55×70 mm.

Shape: Kidney to round shaped.

Margin: Crenate.

Texture: Smooth.

Ribs and veins: None.

Color:

*Upper side.*—Green with redbrown zonation, leaf RHS 146-A, zone RHS 200-A mixed with green. The leaves have some zonation. The zonation becomes more conspicuous when the plant is outside on a cold night. Therefore, in May and September, when the temperature at night tends to be cooler, the plant exhibits better zonation.

*Under side.*—Light green — RHS 146-B.

THE BUD

Size:

*Diameter.*—About 8 mm.

*Length.*—About 8–9 mm at the time of bud opening.

*Shape.*—Ovoid.

*Form.*—Round and thick.

Rate of opening: Quick opening rate of a single flowercup.

Color: When sepals first divide, only the reverse side can be seen. The color of the reverse side is RHS 65-A/B. When petals begin to unfurl, the inside of the petal is seen. The color of inside petal is RHS 70-B.

Sepals: Shiny without hairs.

*Number.*—5.

*Shape.*—Long and pointed.

*Color.*—Inside —glossy light green-RHS 146-C. Outside—medium green-RHS 146-B.

*Form.*—Standing up.

Petiole of floret:

*Length.*—Very short—20–22 mm.

*Strength.*—Erect and arranged hemispherically around the end of the cluster stalk.

*Color.* 13 Dark green-RHS 148-A.

THE FLOWER

Blooming habit: This cultivar is a very early blooming variety (i.e., early April). The blooms are continuous and very floriferous throughout the year, until frost destroys the plants.

Size: Approximately 44 mm in diameter and 10 mm deep.

Borne: In a cluster having between about 39–48 florets per cluster.

Form: Closed cup shape because of the broad petals.

Petals:

*Arrangement.*—Imbricated.

*Form.*—Broad.

*Color.*—Outer petal—Body: mallow purple-RHS 72-D. Base: White with pink spots. Inside petal—Body: mallow purple RHS-72-D. Base: white with pink spots. Reverse side: Purple-RHS 74-D.

*Pattern.*—Substantially the top, two mature petals of each floret variably express a pattern which includes a darker blush-like spot in the central portion of the petal which effuse or bleeds, progressively, into the pink color of the top surface toward the margin. The spot is separated from the attachment point of the petal by a generally white, basal zone of substantially white color, except of the veins, which have the same color as the spot. These markings may be wholly or partly obscured by the overlying petaloids which may or may not express similar color markings. The predominant three outer petals do not express a distinct white spot, but have a distinct red spot which attractively contracts with the fainter mallow purple color of these petals. The bottom petals also have a similar pattern. From a distance, the individual florets of this plant appear to have an unusual star pattern central to the floret.

Texture: Soft.

Appearance: Satiny.

How long do petals remain on stem: About five days.

Petaloids:

*Number.*—About 1 to 2.

*Size.*—Small.

*Color.*—Lavender pink RHS 68-B/C.

Cluster stem:

*Length.*—100–130 mm.

*Color.*—Green-RHS 146-A.

*Characteristics.*—Sturdy and upright.

Persistence: Matured florets or clusters should be picked off.

Disease resistance: This cultivar does not suffer from Botrytis.

Weather resistance: This cultivar does not like very hot or very rainy weather.

Lasting Quality:

*On the cut plant.*—About 25–26 days.

*As a cut flower.*—About 5–6 days.

Fragrance: No perceptible fragrance.

REPRODUCTIVE ORGANS

Stamens:

*Anthers.*—Seven positioned around the ovaries with 1.8 mm length.

*Filaments.*—5 mm in length and white color.

Pollen: Orange in color.

Pistils:

*Number.*—One.

*Length.*—Approximately 6.5 mm.

*Stigmas.*—Pink in color.

Ovaries:

*Color.*—Green.

Seed: Fertile.

*Shape.*—Ovoid.

*Color at maturity.*—Brown-RHS 175-A.

I claim:

1. A new and distinct geranium cultivar substantially as herein shown and described, particularly distinguished by its early appearing lavender-pink flowers with red that appear numerously on upright cluster stems over medium green foliage, said cultivar growing to a height of between 220–240 mm.

* * * * *

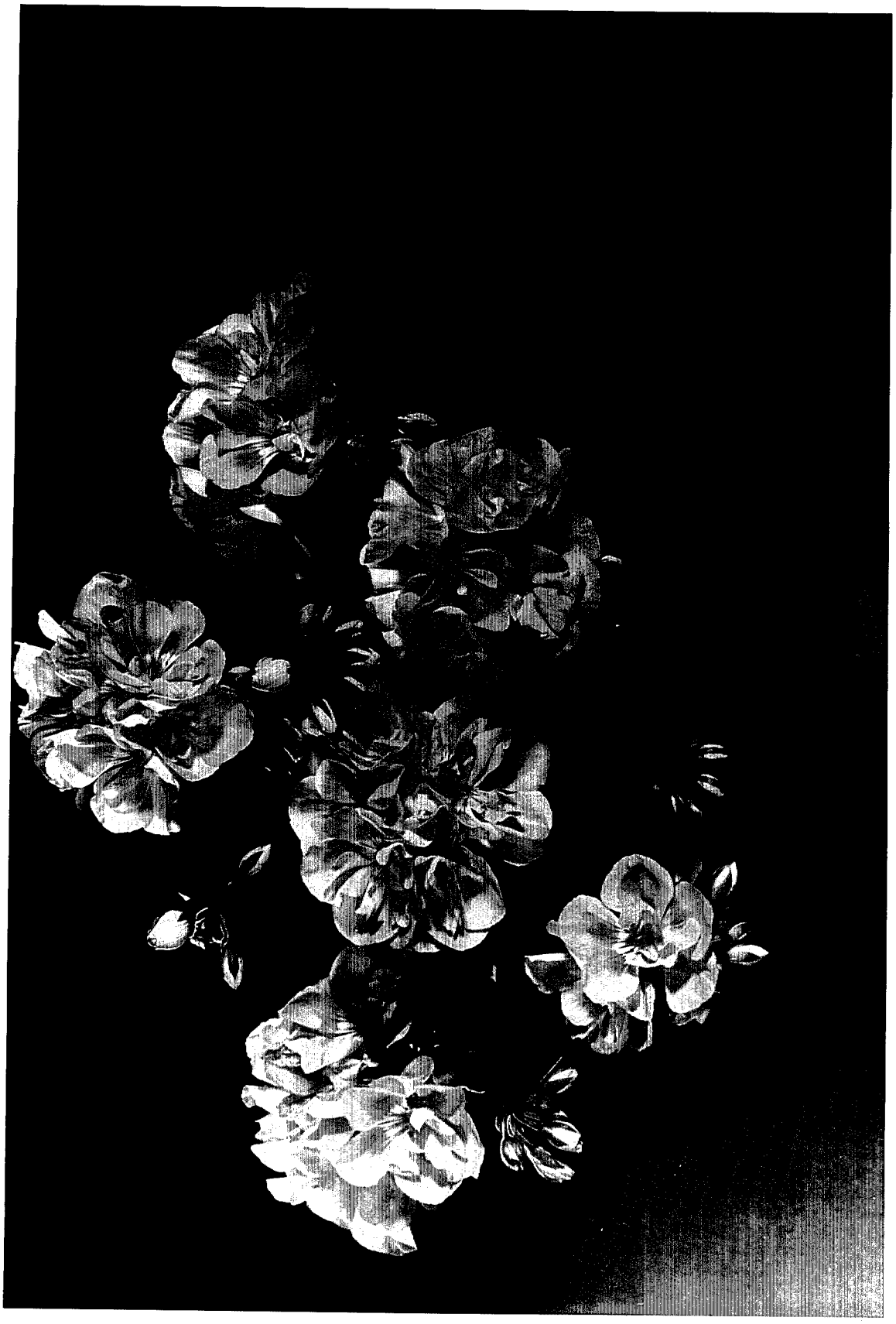

UNITED STATES PATENT AND TRADEMARK OFFICE

CERTIFICATE OF CORRECTION

PATENT NO. : PP 9,203

DATED : July 18, 1995

INVENTOR(S) : Klemm

It is certified that error appears in the above-indentified patent and that said Letters Patent is hereby corrected as shown below:

In column 2, line 19, delete "1922" and insert -- 1992 --.

In column 3, line 15, delete "13".

Signed and Sealed this

Second Day of January, 1996

*Attest:*

Bruce Lehman

BRUCE LEHMAN

*Attesting Officer*

*Commissioner of Patents and Trademarks*